United States Patent [19]

Bowman et al.

[11] Patent Number: 5,767,153
[45] Date of Patent: Jun. 16, 1998

[54] SUSTAINED RELEASE EMULSIONS

[75] Inventors: Lyle M. Bowman, Pleasanton; Rajesh A. Patel, San Mateo; Thomas B. Ottoboni, Belmont, all of Calif.

[73] Assignee: Insite Vision Incorporated, Alameda, Calif.

[21] Appl. No.: 488,675

[22] Filed: Jun. 7, 1995

[51] Int. Cl.⁶ .................... A61K 31/215; A61K 31/19
[52] U.S. Cl. .................... 514/530; 514/573; 514/772
[58] Field of Search .................... 514/530, 573, 514/772

[56] References Cited

U.S. PATENT DOCUMENTS

| 4,347,238 | 8/1982 | Hollingsbee . |
| 4,599,353 | 7/1986 | Bito . |
| 4,883,819 | 11/1989 | Bito . |
| 4,952,581 | 8/1990 | Bito . |
| 5,192,535 | 3/1993 | Davis et al. . |
| 5,340,572 | 8/1994 | Patel et al. . |
| 5,405,846 | 4/1995 | Ueno . |

FOREIGN PATENT DOCUMENTS

| 0063870 | 3/1982 | European Pat. Off. . |
| WO 94/05298 | 3/1994 | WIPO . |
| WO 95/05163 | 2/1995 | WIPO . |

*Primary Examiner*—Zohreh Fay
*Attorney, Agent, or Firm*—Howrey & Simon

[57] ABSTRACT

Ophthalmic methods and compositions are disclosed where particles of the dispersed phase of emulsions are themselves dispersed and stably maintained in physical separation by lightly crosslinked, water swellable polymers present in an aqueous polymeric system formulated for administration to the eye in drop or ribbon form. Medicament is dissolved in that dispersed phase is delivered over a sustained release period.

5 Claims, No Drawings

SUSTAINED RELEASE EMULSIONS

FIELD OF THE INVENTION

This invention relates to topical ophthalmic preparations and methods. More particularly, this invention relates to topical ophthalmic preparations and methods involving medicaments that are not very soluble in aqueous media.

BACKGROUND OF THE INVENTION

Oily drugs such as protoglandins (PGs) have been recognized as useful for the reduction of intraocular pressure if topically applied. Their preferred administration in aqueous solutions has also been recognized. See U.S. Pat. No. 4,952,851. Isotonization agents such as sodium chloride and thickening agents such as carboxyvinyl polymer, together with buffering agents, stabilizers, etc. have also been proposed for their formulation in ophthalmic compositions. Oil diluents for nonaqueous solutions and suspensions have also been proposed. See U.S. Pat. No. 5,405,846.

However, oily drugs present solubility problems in aqueous media, and they are not readily dispersed in such media. Surfactants can be employed to form emulsions in which the oily drugs are dissolved or suspended. See U.S. Pat. No. 4,347,238. However, stability of the emulsion can then become a problem. Over time, oily particles forming the disperse phase of the emulsion can agglomerate or coalesce and separate from the aqueous continuous phase. The presence of salts and/or soluble polymers used to increase viscosity can exacerbate the problem by competing for water, thereby increasing the tendency of the oily disperse phase to separate from the aqueous continuous phase. Indeed, avoidance of large quantities (i.e., greater than 0.3%) of the salt of a lightly cross-linked polyacrylic acid has been recommended because of a tendency to gel the water phase, making the emulsion immobile. See U.S. Pat. No. 4,347,238 at col. 3, lines 7–10.

Furthermore, the irritating effect of ionic surfactants has been said to be a limiting factor on commercialization of ophthalmic compositions in the form of oil-in-water emulsions. See International Publication WO 94/05298 (PCT/US93/00044).

One approach proposed for overcoming some of the foregoing difficulties is the conversion of classical emulsions to submicron emulsions comprising an oil, a phospholipid, a non-ionic surfactant and an aqueous component. Unexplained soothing effects were attributed to the colloidal particles, regardless of whether hydrophobic drugs contained in the particles or hydrophilic drugs soluble in the aqueous component are employed. See WO 94/05298 at application page 8.

Despite the promise of such advantages, potential problems associated with settling of particles and/or their agglomeration might still be encountered. Moreover, such problems could still be exacerbated in the presence of salts and/or soluble polymers used to enhance viscosity.

It would, therefore, be desirable to overcome or ameliorate drawbacks of the sort previously noted, especially when dealing with oily medicaments.

It would also be desirable to enhance the bioavailability of solid medicaments of the type which are only sparingly soluble in water. Such drugs have been satisfactorily dispersed in aqueous polymeric systems of the sustained release type, such as those based on the disclosure of commonly assigned U.S. Pat. No. 5,192,535. However, the bioavailability of the drugs during the sustained release period is inhibited by their weak solubility.

OBJECTS AND SUMMARY

It is a general object of the present invention to provide novel methods and compositions which provide for sustained release aqueous polymeric systems containing emulsions to be advantageously employed in topical ophthalmic applications.

It is another object of the present invention to provide novel methods and compositions wherein the ability to effectively administer oily medicaments is enhanced.

It is an additional object of the present invention to provide novel methods and compositions wherein the tendency of oily medicaments to separate and/or agglomerate in aqueous media is inhibited.

It is a further object of the present invention to provide novel methods and compositions that enhance the ability to effectively use solid medicaments of the type that are only weakly water soluble.

It is yet a further object of the present invention to enhance the bioavailability, during a sustained release period, of such solid medicaments.

The foregoing and other objects and advantages are intended to be realized through preferred forms of the invention wherein particles of the dispersed phase of an emulsion of water and oil and/or lipids, are themselves dispersed and maintain in stable physical separation by a lightly crosslinked, water swellable polymer present in the aqueous polymeric system in an amount in excess of 0.3%, more preferably in excess of 0.5%, by weight of the composition. Preferably, the polymer is polyacrylic acid crosslinked with divinyl glycol.

In the most preferred forms of the invention, the disperse phase of the emulsion contains dissolved medicament selected from oily medicaments (e.g., prostaglandins) and solid medicaments sparingly soluble in water (e.g., 21-aminosteroids).

The pH and osmolality of the composition is adjusted for compatibility with the eye, and a suitable viscosity is established for administration to the eye in drop or ribbon form.

DETAILED DESCRIPTION

In accordance with the present invention, water, an oil and/or lipid, a lightly cross-linked, water swellable polymer, and a medicament are combined in an aqueous system. Particles of the disperse phase of the emulsion are themselves dispersed in that aqueous polymeric system so as to enhance maintenance of the physical separation of such particles.

Rather than using large quantities of the polymer, the present invention relies on including an amount of the polymer sufficient to stably maintain that physical separation of the particles of the disperse phase of the emulsion within the aqueous polymeric system. At least about 0.5% by weight of the total product is preferred. Generally, the range of polymer will be between about 0.5% to about 6.5%, usually about 0.5% to about 2.0%.

The emulsion may be based on oils and/or lipids, with use of lipids being preferred. However, any suitable oils or lipids will suffice. Examples of suitable oils include vegetable oils, mineral oils, medium chain trigliceride oils (which may be a component of vegetable oil), oily fatty acids, and mixtures of any of them. For additional identification of suitable oils, see the disclosures of oils in U.S. Pat. No. 4,347,238 at Col. 3, U.S. Pat. No. 5,405,846 at Col. 6, and International Publication WO 94/05298 at application pages 9–10, which are all hereby incorporated by reference. Preferred lipids are phospholipid compounds or mixtures of phospholipids such as lecithin, phosphatidylcholine, phosphatidyethanolamine or mixtures thereof. See the disclosure of examples of such compounds or mixtures at application page 10 of International Publication WO 94/05298 which is hereby incorporated by reference. Most preferred is a phospholipid emulsion commercially available under the brand name INTRALIPID.

| | |
|---|---|
| Soybean Oil | 10.0 g |
| Phospholipids (from powdered egg yolk) | 1.2 g |
| Glycerin, USP | 2.25 g |
| Water for injection | qs |

The pH of INTRALIPID normally ranges from about 6.0 to about 8.9 but the pH may readily be adjusted in a conventional manner such as by the addition of sodium hydroxide.

Since the lipids already contain hydrophilic functionalities, surfactants may not be necessary or even desirable when lipids alone form the disperse phase of the emulsion. However, surfactants may still be employed; and when oil is a substantial component of the disperse phase of the emulsion, surfactants generally will be employed. Preferred surfactants are non-ionic, and generally a non-ionic oxide condensate of an organic compound which contains one or more hydroxyl groups will be selected. Polysorbate 80 is most preferred. For additional identification of suitable surfactants, see the disclosure of surfactants in U.S. Pat. No. 4,347,238 at column 3 and in the International Publication WO 94/05298 at application pages 10–11 which are hereby incorporated by reference. Generally, the more oil present the more surfactant would be employed. However, the mechanical separation of particles of the disperse phase of the emulsion in the aqueous polymeric system in accordance with the present invention permits use of comparatively less surfactant, thereby reducing irritation potential.

The emulsions employed in carrying out the present invention include both macroemulsions and microemulsions. It is believed that, from the outset of administration and throughout sustained release, macroemulsions whose disperse phase particles are themselves dispersed in the aqueous polymer system will present benefits in being soothing to the eye. However, it is believed that microemulsions will present additional comfort benefits by reason of either the smaller particle size or the previously mentioned, unexplained physiological mechanism mentioned in International Publication WO 94/052989, or both.

The amount of oil and/or lipid which establishes the disperse phase of the emulsion can be varied. Generally, it will range from about 0.1% to about 60% by weight of the entire composition preferably about 1% to about 20% of the entire composition. Surfactants, when employed, will generally amount to less than about 1.0% by weight of the entire composition, preferably in the range of from about 0.001% to about 0.2%.

The aqueous phase of the emulsion will preferably be comprised of distilled water and sodium chloride and will preferably be maintained isotonic with the lacrimal fluid. Osmotic pressure may be adjusted to a pressure of from about 10 to about 400 OsM, more preferably from about 100 to about 300 OsM, and pH will be controlled to be in any range acceptable for administration to the eye, generally a range of about 5.0 to about 9.0. Suitable adjuvants and excipients may also be employed. Typical such additives may include sodium edetate (EDTA), mannitol, sodium hydroxide, and preservatives like benzalkonium chloride (BAK).

The lightly crosslinked polymer systems preferred for use in the present invention are the aqueous suspensions of carboxyvinyl polymers described in U.S. Pat. No. 5,192,535, whose entire disclosure concerning their preparation, characteristics and properties is incorporated herein by reference. However, any other suitable lightly crosslinked, water soluble polymer may be employed, for example, polyhydroxyethylmethacrylate or polyvinyl pyrolidone. The amount of water swellable polymer will preferably range from greater than 0.3% to about 6.5% by weight and preferably from about 0.5% to about 4.5% by weight, and more preferably from about 1.0% to about 2.0% of the total composition. Most preferably, the polymer is polycarbophil, a polyacrylic acid polymer lightly crosslinked with divinyl glycol.

The viscosity of the aqueous suspension of the polymer will be desirably adjusted in a conventional manner to be in a range suitable for convenient administration to the eye in drop or ribbon form. Generally, that viscosity will be in the range of about 1,000 to about 100,000 centepoises.

It is envisioned that certain benefits of the present invention can be realized independently of the medicament and its solubility. Overall, drug content will vary, usually from about .001% to about 10%, by weight of the entire composition.

In its most preferred form, however, the benefits of the present invention will be realized through implementation with oily drugs that are dissolved in the oil and/or lipid. Prostaglandins and derivatives thereof are especially preferred medicaments envisioned for use, alone or in combination therapy, in that implementation of the present invention. As used herein, the term oily medicament means a medicament that is hydrophobic and that is liquid at physiological pH, temperature and osmolality. The freebase form of pilocarpine also constitutes an oily drug. Other examples will be recognized by those skilled in the art.

Prostaglandins (PGs) were initially isolated from sheep seminal vesicles and human seminal fluid but may be found in most mammalian tissues. They are a group of eicosanoids which contain cyclical fatty acids, including chain moities, and are known to possess diverse biological activities. These activities include stimulation of smooth muscle, dilation of small arteries, bronchial dilation, and lowering of blood pressure, among others.

The primary PGs are classified based on the structural feature of a 5-membered cyclical moiety into PGAs, PGBs, PGCs, PGDs, PGEs, PGFs, PGGs, PGHs, PGIs, and PGJs. They are further classified based on the presence or absence of unsaturation and oxidation in the chain moiety using subscripts 1, 2 and 3 to designate the location of unsaturation and oxidation. They are further subclassified according to the configuration of a hydroxy group into alpha and beta configurations. The chemical structure and classification of these compounds are known and are described, for instance, in U.S. Pat. No. 5,405, 846, the disclosure of which is incorporated herein by reference. Other patents describing prostaglandins and their use, either alone or in combination with other medicaments, are disclosed in the above-referenced patent and in U.S. Pat. No. 4,599,353; U.S. Pat. No. 4,952, 581; and U.S. Pat. No. 4,883,819; the disclosures of which are incorporated herein by reference.

As the foregoing patents indicate, prostaglandins and their derivatives and conjugates are particularly useful for the reduction of intraocular pressure when applied to the surface of the eye. Moreover, prostaglandins may be combined with other drugs, such as adrenergic blocking agents, to relieve intraocular pressure. It is contemplated that any of the prostaglandins and their derivatives and conjugates may be used alone or in combination with other drugs in accordance with the present invention. Formulations of the present inventions incorporating prostaglandins, either alone or in combination with other drugs, are particularly useful for the reduction of intraocular pressure caused by chronic glaucoma.

The amount of any oily medicament employed will vary depending on solubility in the disperse phase of the emulsion. Complete solubility is preferred. In addition, use of an amount of oily medicament that would establish a saturated solution in the given quantity of oil and/or lipid could be desirable. However, consideration of activity and irritation propensity will also govern the medicament content. For example, prostaglandins are irritating at high concentrations in the eye and have high activity at low concentrations, so an amount of 0.005% or less, down to about 0.001% is preferred.

Especially significant benefits of the present invention are also envisioned where the medicament is a solid drug that is only weakly soluble in water, but quite soluble in the oil and/or lipid. Such drugs, for example, fluoromethalone, have been satisfactorily suspended in aqueous polymeric suspensions of polycarbophil for sustained delivery. However, when dissolved in the oil and/or lipid in accordance with the present invention, their bioavailability to the targeted issue may be enhanced. Since dissolution from a solid is not then required, the transfer rate into an aqueous phase may be enhanced so a higher permeation may be achieved, thereby by presenting a higher concentration of dissolved drug to the targeted tissue during the sustained release. Other examples of solid drugs which are weakly soluble in water, and whose bioavailability can be similarly enhanced by dissolution in the oil and/or lipid, will be recognized and appreciated by those skilled in the art.

The following Table I provides examples of compositions that can be used to administer oily medicaments alone or in combination therapy in accordance with the present invention.

TABLE I

OILY COMPOUNDS/COMBINATIONS
Composition
Weight %

| Component | Example 1 | Example 2 | Example 3 | Example 4 | Example 5 |
|---|---|---|---|---|---|
| PGF$_{2\alpha}$-1-Isopropyl Ester | 0.005 | — | — | 0.005 | 0.005 |
| Pilocarpine | — | 2.0 | — | — | — |
| Scopolamine | — | — | 0.25 | — | — |
| Levobunolol HCl | — | — | — | 0.1 | — |
| Timolol Maleate | — | — | — | — | 0.25 |
| EDTA | 0.1 | 0.1 | 0.1 | 0.1 | 0.1 |
| Sodium Chloride | 0.2 | — | 0.2 | 0.2 | 0.2 |
| Mannitol | — | 2.0 | — | — | — |
| Polycarbophil | 1.2 | 1.15 | 1.15 | 1.2 | 1.2 |
| Oil/Lipids | 1 | 5 | 10 | 5 | 5 |
| BAK | 0.005 | 0.005 | 0.005 | 0.008 | 0.008 |
| Sodium Hydroxide | q.s. | q.s. | q.s. | q.s. | q.s. |
| Purified Water | q.s. 100 | q.s. 100 | q.s. 100 | q.s. 100 | q.s. 100 |
| pH | 6.0 | 5.4 | 5.5 | 6.0 | 6.0 |

| Component | Example 6 | Example 7 | Example 8 | Example 9 |
|---|---|---|---|---|
| 21-Aminosteroid (U74006F) | 0.25 | — | — | — |
| Batismastat-* | — | 0.3 | — | — |
| Fluorometholone | — | — | 0.1 | — |
| Lexipfant-** | — | — | — | 0.3 |
| EDTA | 0.1 | 0.1 | 0.1 | 0.1 |
| Sodium Chloride | 0.2 | 0.2 | 0.2 | 0.2 |
| Polycarbophil | 1.0 | 1.15 | 1.2 | 1.3 |
| Oil/Lipids | 20 | 10 | 10 | 20 |
| BAK | 0.005 | 0.005 | 0.005 | 0.005 |
| Polysorbate 80 | 0.2 | — | — | — |
| Sodium Hydroxide | q.s | q.s | q.s | q.s |
| Purified Water | q.s 100 | q.s 100 | q.s 100 | q.s 100 |
| pH | 6.0 | 6.0 | 5.6 | 6.0 |

*The chemical name is: [4-(N-hydroxyamino)-2R-isobutyl-3S-(thienylthiomethyl)-succinyl]-L-phenylalanine-N-methylamide
**The chemical name is: (S)-4-methyl-2-{methyl-[4-(2-methyl-imidazo{4,5-c}pyridin-1-ylmethyl)-benzenesulfonyl]-amino}-pentanoic acid ethyl ester The Examples 1–9 listed in Table I can be prepared on a 100gm scale in the following manner:

1. An oil phase containing triglyceride, oily medicament or water insoluble drug, and lipid is heated to about 50° C.

2. An aqueous phase, containing water, isotonic agent, EDTA, and water soluble non-ionic surfactant, is heated to about 50° C.

3. The two phases are combined together, mixing well with a magnetic stirrer to produce a coarse emulsion. The emulsion is further heated to about 80° C.

4. The emulsion is homogenized by a homogenizer at 10,000 rpm for 3 minutes and then rapidly cooled to below 40° C. in an ice bath.

5. After cooling, the emulsion is sonicated by a probe ultrasonic processor for 5–10 minutes until a translucent microemulsion is obtained. The pH adjustment to the target pH is made after the sonication step.

6. A polymer system is prepared separately by hydrating the polymer in water and then adding EDTA, isotonic agent, and water soluble drug.

7. The pH of the polymer system is adjusted to target pH of the formulation with NaOH.

8. The microemulsion is added to the polymer system and these components are mixed.

The foregoing Examples are illustrative and are not to be considered limiting of the present invention. Departure from specifics set forth either in those examples or elsewhere herein can be made without departing from the spirit and scope of the invention as defined in the appended claims.

What is claimed is:

1. A method of preparing a sustained release topical ophthalmic composition for administration of an oily medicament or solid medicament sparingly soluble in water to the eye comprising:

dissolving a least some of the oily medicament or solid medicament sparingly soluble in water in the disperse phase of an oil, lipid or oil and lipid emulsion, dispersing the disperse phase of the oil, lipid or oil and lipid emulsion which has such medicament dissolved therein in an aqueous suspension of a lightly crosslinked, water swellable polymer present in an amount in excess of 0.3% by weight of the composition adjusting the pH and osmolality for compatibility with the eye, and establishing a viscosity of the system for administration to the eye in drop or ribbon form.

2. The method according to claim 1, wherein said polymer is present in an amount in the range of about 0.5% to about 6.5% by weight of the composition.

3. The method according to claim 2, wherein said polymer is present in an amount in the range of about 0.5% to about 2% by weight of the composition.

4. The method according to claim 1, wherein said polymer is present in an amount in the range of about 0.5% to about 6.5% by weight of the composition.

5. The method according to claim 4, wherein said polymer is present in an amount in the range of about 0.5% to about 2% by weight of the composition.

* * * * *